United States Patent [19]

Orvik et al.

[11] Patent Number: 5,012,017

[45] Date of Patent: Apr. 30, 1991

[54] PHENOXYPHENOXYPROPIONATES, INTERMEDIATES THEREOF AND METHODS OF PREPARATION

[75] Inventors: Jon A. Orvik; Norman R. Pearson, both of Walnut Creek, Calif.; Anthony P. Haag, Midland, Mich.; Timothy J. Adaway, Midland, Mich.; Larry D. Kershner, Midland, Mich.; Andrew S. Kende, Pittsford, N.Y.

[73] Assignee: DowElanco, Indianapolis, Ind.

[21] Appl. No.: 313,665

[22] Filed: Feb. 21, 1989

Related U.S. Application Data

[63] Continuation-in-part of Ser. No. 233,385, Aug. 18, 1988, abandoned, which is a continuation-in-part of Ser. No. 138,279, Dec. 28, 1987, abandoned.

[51] Int. Cl.$^5$ .............................................. C07C 37/00
[52] U.S. Cl. ........................................ 568/803; 560/62
[58] Field of Search ................................ 568/804, 803

[56] References Cited

U.S. PATENT DOCUMENTS

| | | | |
|---|---|---|---|
| 3,721,703 | 3/1973 | Nahm et al. | 260/471 |
| 3,875,247 | 4/1975 | Bourdin et al. | 568/803 |
| 3,927,122 | 12/1975 | Bourdin et al. | 568/803 |
| 3,927,123 | 12/1975 | Bourdin et al. | 568/803 |
| 3,954,442 | 5/1976 | Becker et al. | 71/108 |
| 4,238,626 | 12/1980 | Nahm et al. | 562/472 |
| 4,252,980 | 2/1981 | Koch et al. | 560/21 |
| 4,276,080 | 6/1981 | Koerwer | 71/108 |
| 4,301,295 | 11/1981 | Nahm et al. | 560/62 |
| 4,309,547 | 1/1982 | Koch et al. | 546/301 |
| 4,332,960 | 6/1982 | Trosken et al. | 560/62 |
| 4,370,489 | 1/1983 | Boesenberg et al. | 560/62 |
| 4,391,995 | 7/1983 | Nahm et al. | 568/637 |
| 4,465,872 | 8/1984 | Suzuki et al. | 568/803 |
| 4,531,969 | 7/1985 | Nestler et al. | 71/108 |
| 4,532,328 | 7/1985 | Kleschick | 546/302 |

FOREIGN PATENT DOCUMENTS 1577181 3/1976 United Kingdom .
1593167 12/1977 United Kingdom .

OTHER PUBLICATIONS

Hassell, C. H., Organic Reactions, 1957, 9, Chapter 3, pp. 73–106.
De la Mare, P. B. D., Electrophilic Halogenation, 1976, p. 131f.
Schubert, W. M. et al., J. American Chemical Society, 97 (13), pp. 3877–3878, 1975.

*Primary Examiner*—Paul J. Killos
*Attorney, Agent, or Firm*—Craig E. Mixan; Ronald G. Brookens

[57] ABSTRACT

A method for preparing substituted phenoxyphenols which are useful in the preparation of herbicidal (phenoxyphenoxy)propionates is disclosed. The process involves the oxidation of substituted phenoxyphenones to the corresponding phenoxyphenyl esters and their conversion to the desired phenoxyphenol. Novel intermediates for the process are similarly disclosed.

9 Claims, No Drawings

PHENOXYPHENOXYPROPIONATES, INTERMEDIATES THEREOF AND METHODS OF PREPARATION

CROSS-REFERENCE TO RELATED APPLICATION

This application is a continuation-in-part of the copending application Ser. No. 233,385, filed Aug. 18, 1988, now abandoned which is a continuation-in-part of application Ser. No. 138,279, filed Dec. 28, 1987, now abandoned.

FIELD OF THE INVENTION

The present invention relates to methods for preparing (phenoxyphenoxy)propionate compounds, and to certain novel intermediates thereof. More particularly, the present invention relates to methods for preparing brominated (phenoxyphenoxy)propionate derivatives.

BACKGROUND OF THE INVENTION

Various (phenoxyphenoxy)propionate compounds are known to possess herbicidal and plant-growth regulating properties. For example, see U.S. Pat. Nos. 3,954,442; 4,550,192; 4,332,961; 4,332,960; 4,370,489; 4,276,080 and British Patent Specification 1,577,181. Also, methods for preparing enantiomers are described in U.S. Pat. Nos. 4,531,969 and 4,532,328. In U.S. Pat. No. 4,252,980 a method is taught for preparing the methyl ester.

Of particular interest among the (phenoxyphenoxy)propionate herbicides are the 2-(4-(2'-halo-4'-bromophenoxy)phenoxy)propionates which exhibit particularly desirable properties as described in U.S. Pat. Nos. 4,370,489: 4,531,969; and 4,550,192.

Processes for making selected intermediates used to prepare (phenoxyphenoxy)propionates are taught in U.S. Pat. Nos. 3,721,703; 4,238,626; 4,252,980; 4,301,295: 4,309,547 and 4,391,995. Although these processes are effective, a number of them utilize diazonium reactions which are potentially explosive when employed on an industrial scale. It is desirable to find methods for preparing phenoxyphenoxy compounds which are as safe as or safer than those previously taught. It is also desirable to find a method which employs a fewer number of steps than other known processes. It is also desirable to find methods where yields are as good as or better than previously known processes.

SUMMARY OF THE INVENTION

The present invention is directed to the preparation of (phenoxyphenoxy)propionate compounds and to novel intermediates useful in their preparation.

More specifically, the present invention is directed to the preparation of and to novel phenoxyphenones of the formula:

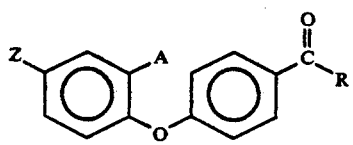

wherein
Z is bromine (Br) or hydrogen (H);
A is halogen and
R is H, C-1 to C-10 alkyl, phenyl or substituted phenyl of the formula

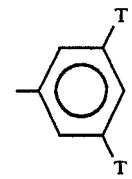

wherein T is independently halogen or H.

The present invention is also directed to the preparation of and to novel phenoxyphenyl ester compounds of the formula:

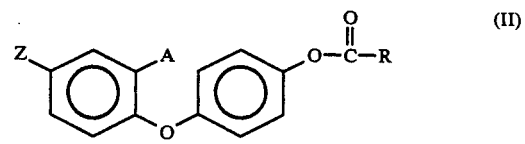

wherein
Z is bromine (Br) or hydrogen (H);
A is halogen; and
R is H, C-1 to C-10 alkyl, phenyl or substituted phenyl of the formula

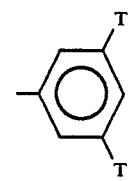

wherein T is halogen or H.

In a further embodiment, the present invention is also directed to selective bromination methods for the preparation of brominated compounds of the formula

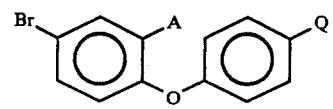

wherein

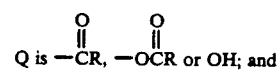

A and R are as previously defined.

As used herein, "halogen" refers to fluorine, chlorine, bromine and iodine.

Such phenoxyphenones and phenoxyphenyl esters are valuable intermediates in the preparation of (phenoxyphenoxy)propionate compounds useful as herbicides and plant growth regulators.

The present invention has the advantage of providing a method for preparing (phenoxyphenoxy)propionate compounds in yields as good as or better than other known methods. The present invention also has the advantage of providing a method which is as safe as or safer than other methods previously taught. Another advantage is that it provides a method for preparing (phenoxyphenoxy)propionates in purity as good as or better than other known methods And still yet another advantage is that it provides a method which reduces the number of steps needed to prepare (phenoxyphenoxy)propionate compounds compared with other known methods. And still yet another advantage is that it provides novel and useful intermediates for use in such methods. The same advantages apply to the optically active R-enantiomers.

DETAILED DESCRIPTION OF THE INVENTION

The phenoxyphenols of Formula (III)

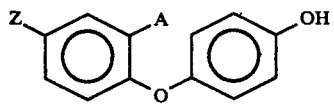

wherein
Z is Br or H: and
A is halogen
are key intermediates in the preparation of 2-(4-(2'-halo-4'-bromophenoxy)phenoxy)propionate herbicides. The present invention is directed to a novel method for the preparation of phenoxyphenols of Formula (III) from phenoxyphenones of Formula (I). The process is illustrated in the following steps (a) and (b). Under certain situations, the oxidation (step (a)) and the acid hydrolysis (step (b)) can effectively be conducted as one step, in situ.

Step (a): Oxidation

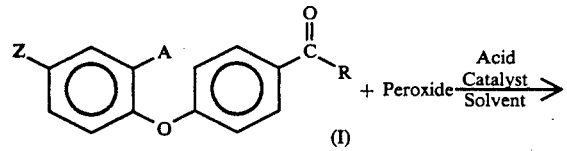

Step (b): Hydrolysis/Alcoholysis

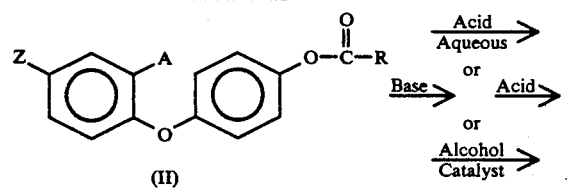

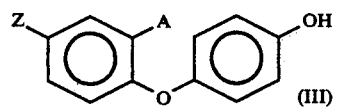

The phenoxyphenone starting materials of Formula (I) can be prepared by a variety of procedures. For example, a substituted phenol can be contacted with a phenylcarbonyl compound in the presence of a base and solvent under conditions effective to give the desired phenoxyphenone of Formula (I). The reaction is exemplified as follows:

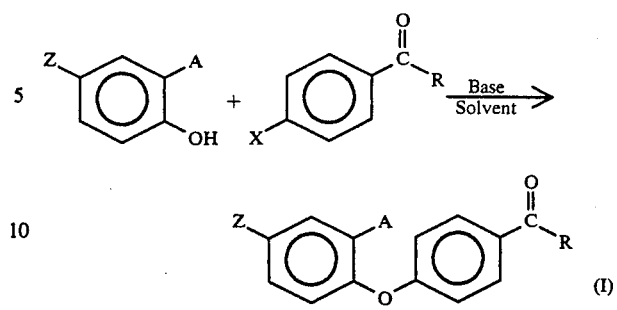

wherein
Z is Br of H;
Z is halogen;
X is halogen; and
R is H, C-1 to C-10 alkyl, phenyl or substituted phenyl of the formula

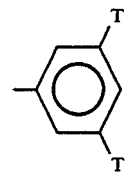

wherein T is independently halogen or H.

With respect to the phenol, Z is preferably hydrogen and A is preferably fluoro or chloro. With respect to the phenylcarbonyl compound, X is preferably fluoro or chloro and R is C-1 to C-10 alkyl or phenyl.

The phenol can be contacted with the phenylcarbonyl compound in molar ratios ranging from stoichiometric (i.e., 1:1) to a slight excess (i.e., 2-3 percent) of either reactant.

Suitable bases for contacting the phenol and the phenylcarbonyl compound include the bases of alkali and alkaline earth metals such as sodium hydroxide (NaOH), potassium hydroxide (KOH), sodium carbonate ($Na_1CO_3$), potassium carbonate ($K_2CO_3$) and the hydroxides and carbonates of magnesium or lithium. Other bases also include sodium or potassium methoxide.

The molar ratio of base to phenol can be in the range from about 1:1 to an excess of about 10:1 (base:phenol), preferably in amounts of slight excess over stoichiometric, e.g., 1.1-1.5:1.

Suitable inert organic solvents which can be employed include polar aprotic solvents such as N-methylpyrrolidone (NMP), dimethylsulfoxide (DMSO), hexamethylphosphoramide (HMPA), sulfolane, acetonitrile or mixtures thereof.

The reactants can be contacted at temperatures ranging from ambient to about 250 degrees Centigrade (° C.), preferably from about 50° to 190° C. The reactants are contacted for a time sufficient to ensure substantial completion of the reaction, ranging from about 15 minutes (min) to 24 hours (hr) or more. The contacting is carried out at ambient pressures, although pressures greater than ambient can be employed.

The contacting of the reactants can be carried out in the presence of air, although in order to reduce by-product formation, the contacting is preferably carried out under an inert atmosphere such as that provided by nitrogen, helium or argon, preferably nitrogen.

Antioxidants can be employed in the reaction mixture to reduce by-product formation. Such antioxidants include t-butylcatechol, benzothiazine, butylated hydroxytoluene (BHT), butylated hydroxyanisole (BHA) or mixtures thereof. The amount of antioxidant employed in the reaction mixture can range from about 0.1 to about 10 percent (%) by weight of either the phenol (I) or phenyl carbonyl reactant preferably about 2 percent.

The requisite phenols are known compounds and can be prepared, for example, as described in U.S. Pat. No. 4,550,192. Appropriate phenyl carbonyl compounds can be prepared, for example, by the processes taught by N. BuuHoi and P. Jacquignon in *Rec. Trav. Chim.* 68, 781–8 (1949) or analogous procedures thereof.

Alternatively, when R is C-1-C$_{10}$ alkyl, phenyl or substituted phenyl of the formula

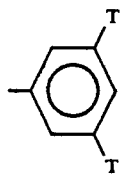

wherein T is independently halogen or H, the phenoxyphenones of Formula (I) may be prepared by the conventional Friedel-Crafts acylation of the appropriate diphenyl ether with an acyl halide in the presence of a Lewis acid catalyst according to the following reaction:

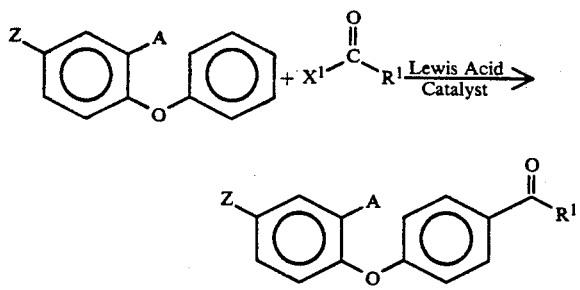

wherein
Z is Br or H:
A is halogen;
X$^1$ is halogen; and
R$^1$ is C1–C10 alkyl, phenyl or substituted phenyl of the formula

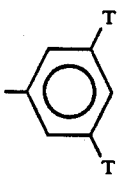

wherein T is independently halogen or H.

With respect to the diphenyl ether, Z is preferably hydrogen and A is preferably fluoro or chloro. With respect to the acyl halide, X$^1$ is preferably chloro or bromo and R$^1$ is preferably substituted phenyl of the formula

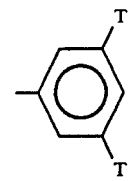

wherein T is independently halogen or H.

The diphenyl ether can be contacted with the acyl halide in molar ratios ranging from stoichiometric (i.e., 1:1) to a slight excess (i.e., 2–3 percent) of either reactant.

Suitable Lewis acid catalysts include the chlorides of aluminum, iron, tin, antimony and boron. A little more than one mole of catalyst per mole of acyl halide is required since the first mole of catalyst coordinates with the oxygen of the acylating reagent.

Suitable inert solvents which can be employed include polar solvents such as nitrobenzene and nonpolar solvents such as methylene chloride, chloroform and carbon tetrachloride.

The reactants can be contacted at temperatures ranging from about 0° to about 200° C., preferably from about 0° to about 100° C. The reactants are contacted for a sufficient time to ensure substantial completion of the reaction, ranging from about 15 min to 24 hr or more. The contacting is carried out at ambient pressure, although pressures greater than ambient can be employed.

The requisite diphenyl ether can be prepared, for example, by the Ullmann diaryl ether synthesis. Appropriate acyl halides can be prepared by the reaction between the corresponding acid and an inorganic acid halide such as, for example, thionyl chloride.

The desired phenoxyphenone (I), prepared from either the phenol and phenylcarbonyl or the diphenyl ether and acyl halide starting materials can be recovered by conventional procedures such as distillation, recrystallization, phase separation or extraction from water into a water-immiscible organic solvent such as methylene chloride, perchloroethylene, carbon tetrachloride (CCl$_4$) or chloroform (CHCl$_3$). The phenoxyphenone can be further purified by repeating the above procedures or can be used in its unpurified form for subsequent reactions.

By following the preparative procedures as set forth in the examples herein and by employing the appropriate starting materials or reactants, the following compounds are prepared, as set forth in Table 1.

TABLE 1

| Z | A | R |
|---|---|---|
| H | H | Φ(phenyl) |
| H | F | Φ |
| H | F | CH$_3$ |
| H | F | H |

TABLE 1-continued

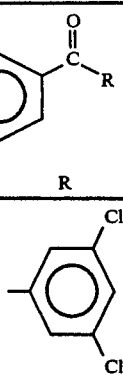

| Z  | A  | R            |
|----|----|--------------|
| H  | F  | 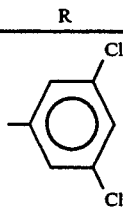 |
| Br | F  | Φ            |
| Br | F  | CH₃          |
| Br | F  | H            |
| H  | Cl | Φ            |
| H  | Cl | CH₃          |
| H  | Cl | H            |
| Cl | Cl | Φ            |
| Cl | Cl | CH₃          |
| Cl | Cl | H            |
| Br | Cl | Φ            |
| Br | Cl | CH₃          |
| Br | Cl | H            |

Step (a): Oxidation

In Step (a) of the process overall, the phenoxyphenone of Formula (I) is contacted with a peroxide in the presence of an acid catalyst to give the desired phenoxyphenyl ester of Formula (II). The reaction is exemplified as follows:

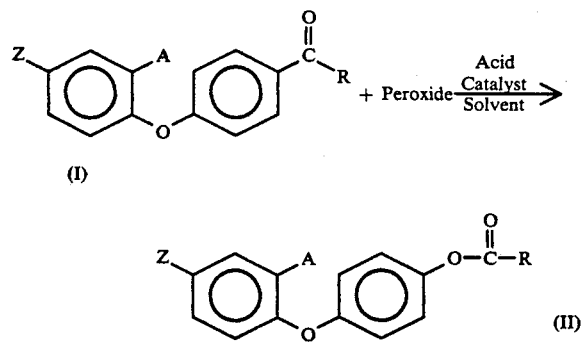

wherein Z, A, and R are as defined hereinbefore.

Peroxides which can be employed include hydrogen peroxide (HOOH) alone or peracetic acid (CH₃COOOH) alone: the peroxide can also be mixtures of hydrogen peroxide with either acetic acid (CH₃COOH) or peracetic acid. Where a mixture of hydrogen peroxide and acetic acid is employed, the acetic acid is employed to regenerate additional peracetic acid for reaction with the phenoxyphenone of Formula (I). The peroxide is employed in amounts ranging from about 1 to about 10, preferably from about 1.1 to about 2.0 moles peroxide to 1 mole phenoxyphenone (I).

Where a mixture of hydrogen peroxide and acetic acid is employed, the ratio of acetic acid to peroxide can vary, ranging from about 100 or more moles acetic acid per mole of peroxide to about 1 mole acetic acid per mole of peroxide: preferably ratios from about 15:1 (moles acetic acid:moles peroxide) to about 2:1 are employed.

In the situation where peroxide is contacted with the phenoxyphenone (I) without acetic acid in amounts sufficient to oxidize the phenoxyphenone (I) to the desired phenoxyphenyl ester (II), such amounts can range from about 10 to about 1.1 moles peroxide per mole phenoxyphenone (I). A slight stoichiometric excess of peroxide in the range of about 1.2-2:1 (moles peroxide:moles phenoxyphenone) is preferred.

The acid catalyst in the process of Step (a) can be any acidic catalyst which will catalyze the oxidation of the phenoxyphenone of Formula (I) by the peroxide to yield the phenoxyphenyl ester of Formula (II). Such acid catalysts include mineral acids such as sulfuric acid (H₂SO₄), phosphoric acid (H₃PO₄) or organic acids such as acetic acid or acidic ion exchange resins such as Dowex ® MSC-1-H ion exchange resin (trademark of The Dow Chemical Company).

The acid catalyst is employed in an amount ranging from about 0.1 to 100 moles acid catalyst per mole phenoxyphenone (I), preferably about 1-3:1 (moles acid catalyst:moles phenoxyphenone).

The process of Step (a) can be conducted neat although a slight amount to an excess of inert solvent can be employed to dissolve any starting materials in solid or crystalline form. Solvents which can be employed include the C1-C6 alcohols, such as methanol, ethanol, butanol, hexanol, and the like. Other solvents include acetonitrile.

Acetic acid which can serve as both a reactant and as a solvent, can be employed in excess amounts relative to the phenoxyphenone (I).

The process of Step (a) is conducted at temperatures, pressures, and times effective to convert the phenoxyphenone of Formula (I) to the phenoxyphenyl ester of Formula (II). Such temperatures can range from about 0° C. to about the temperatures which would cause significant decomposition of the peroxide, preferably from 0° to about 80° C., more preferably from about 0° to about 60° C., most preferably from about 20° to 50° C. The process of Step (a) can be conducted at pressures greater than ambient, although ambient pressures are preferred.

The ingredients in Step (a) can be contacted in any particular order. Preferably, though, the phenoxyphenone, solvent and acid catalyst of Step (a) are first contacted together followed by subsequent additions of small amounts of peroxide, due to the highly exothermic reaction of the peroxide in the reaction medium.

The desired phenoxyphenyl ester of Formula (II) can be recovered by conventional techniques such as extraction and/or distillation. For example, the reaction medium can be diluted with water and the organic phase containing the desired phenoxyphenyl ester (II) can be separated from the aqueous phase Further purification can be accomplished by subsequent distillation, crystallization or the like.

Step (b): Hydrolysis/Alcoholysis

The phenoxyphenyl ester of Formula (II) can be converted to the desired phenoxyphenol of Formula (III) by three alternative methods.

Alternative 1 - In-Situ Acid Hydrolysis

In the in-situ acid hydrolysis, the phenoxyphenone (I) is converted directly to the phenoxyphenol (III). The phenoxyphenyl ester (II) is hydrolyzed in the aqueous acidic reaction media without isolation according to the following scheme:

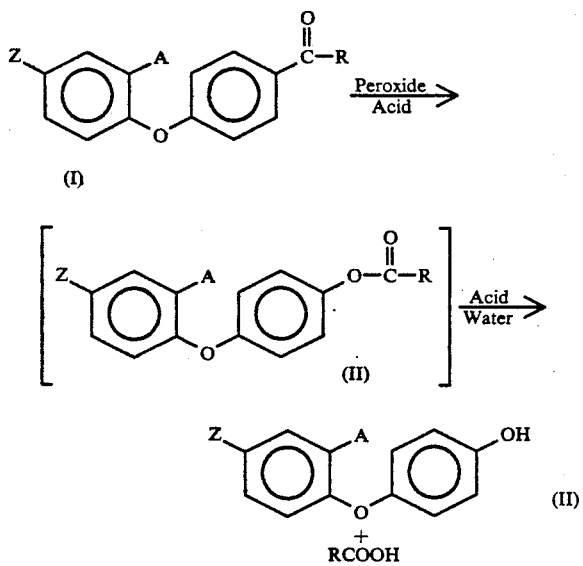

wherein Z, A and R are as defined hereinbefore.

The hydrolysis of the phenoxyphenyl ester (II) to the desired phenoxyphenol (III) occurs in-situ during Step (a) when sufficient acid is present, so that an additional separate contacting step such as in Alternatives 2 and 3 is not essential in order to prepare the desired phenoxyphenol (III). Generally, such amounts can range from stoichiometric to excess acid, preferably a slight excess. Acids which can be employed for hydrolysis include mineral acids such as sulfuric acid ($H_2SO_4$), hydrochloric (HCl), phosphoric ($H_3PO_4$) or organic acids such as acetic acid, toluene sulfonic acid, acidic ion exchange resins, such as Dowex® MSC-1-H.

During Step (a) wherein for the phenoxyphenone (I) R is phenyl or

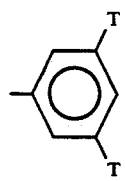

higher temperatures may be required than is needed for the hydrolysis where R is H or alkyl. Excess or residual peroxide need not be removed prior to the hydrolysis, although preferably, any residual or excess peroxide present with the phenoxyphenone (1) and/or phenoxyphenyl ester (II) is neutralized prior to hydrolysis to the phenoxyphenol (III). Any residual peroxide can be neutralized by adding a stoichiometric amount of a reducing agent such as sodium sulfite or sulfur dioxide. Following neutralization of the peroxide, the phenoxyphenyl ester (II) wherein R is phenyl or

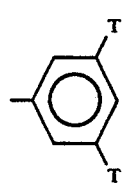

is hydrolyzed in-situ by elevating the temperature of the reaction medium to a temperature effective to hydrolyze the phenoxyphenyl ester (III), generally between about 100° to about 200° C.

Recovery of the desired phenoxyphenol (III) prepared from the phenoxyphenone (I) and/or phenoxyphenyl ester (II) wherein R is H or alkyl can be accomplished by extraction procedures. After reaction, water and optionally, a water-immiscible organic solvent is added to the reaction medium, followed by separation of the organic phase containing the desired phenoxyphenol (III) and distillation thereof. Alternatively, the reaction medium can be diluted with water followed by crystallization and filtration to recover the desired phenoxyphenol (III).

Recovery of the desired phenoxyphenol (III) prepared from the phenoxyphenone (I) and/or phenoxyphenyl ester (II) wherein R is phenyl or

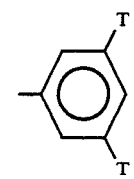

can be accomplished by dilution of the reaction medium with water and separation of the organic phase. The organic phase is washed with a stoichiometric amount of a base in quantities sufficient to convert the residual organic acids such as benzoic acids to their corresponding salts and yet maintain the desired phenoxyphenol (III) in its protonated form. For example, the pH can be adjusted to about 5.5–8.0 and the desired phenoxyphenol (III) can then be recovered by phase separation.

Alternative 2 - Base Hydrolysis

In alternative method 2, the phenoxyphenyl ester (II) is contacted with an aqueous base to give the phenoxyphenate (III'), followed by subsequent contacting with a suitable acid in amounts effective to yield the desired phenoxyphenol (III) as follows:

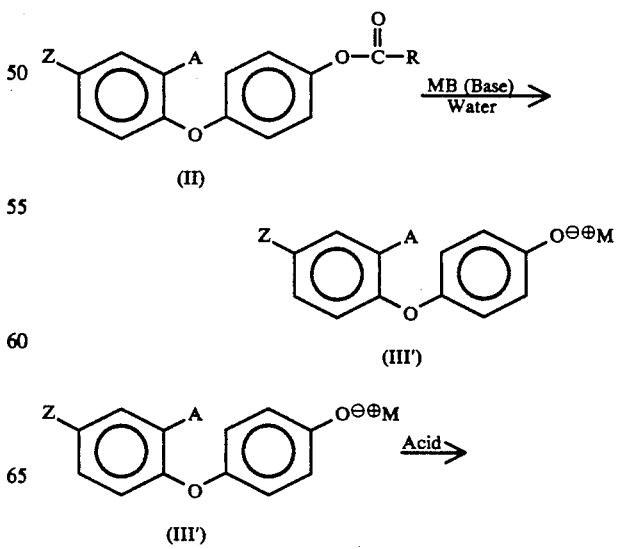

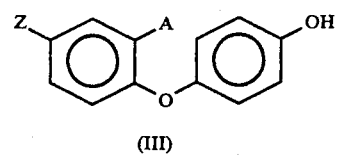

(III)

wherein Z, A and R are as defined hereinbefore.

The bases (MB) employed for converting the phenoxyphenyl ester (II) to the phenoxyphenate salt (III') include the carbonate or hydroxide bases of the alkali and alkaline earth metals such as sodium, potassium or lithium; preferably, the hydroxide bases are employed. The base can also be anhydrous sodium or potassium methoxide. A molar excess of base relative to the phenoxyphenyl ester (II) is used to cleave the phenoxyphenyl ester (II) to the phenoxyphenolate (III'). Preferably two or more moles of base are contacted with the phenoxyphenyl ester (II).

Inert solvents can be employed in amounts sufficient to dissolve the phenoxyphenyl ester (II), the base or both. Suitable solvents include non-acidic solvents such as C-1 to C-6 alcohols including methanol, ethanol, propanol, hexanol and the like, aromatic hydrocarbons such as toluene and chlorobenzene: chlorinated hydrocarbons such as methylene chloride, carbon tetrachloride, perchloroethylene and the like; and polar solvents such as dimethylsulfoxide (DMSO), tetrahydrofuran and sulfolane.

The temperatures, pressures and times employed should be sufficient to yield the desired phenoxyphenolate (III'). Such temperatures can range from about 0° to about 100° C., preferably from about ambient to the melting point of the phenoxyphenyl ester (II). Ambient pressures are preferred although pressures greater than ambient can be employed. The times for contacting of the ingredients can vary from about one hour to 24 hours or more.

The phenoxyphenolate (III') can be converted to the desired phenoxyphenol (III) by contacting the phenoxyphenolate (III') with sufficient acid to bring the pH of the reaction medium to a pH less than or equal to about 6. Generally, such amounts can range from stoichiometric to excess acid, preferably a slight excess. Acids which can be employed for converting the phenoxyphenolate (III') to the desired phenoxyphenol (III) include mineral acids such as $H_2SO_4$, HCl, $H_3PO_4$, or organic acids such as acetic acid, toluenesulfonic acid or acidic ion exchange resins such as those described hereinbefore. The desired phenoxyphenol can be recovered by extraction, filtration and/or phase separation methods described hereinbefore.

Alternative 3 - Alcoholysis (Transesterification)

In another alternative method, the phenoxyphenyl ester (II) is contacted with an alcohol (R'OH) in the presence of a transesterification catalyst to yield the desired phenoxyphenol (III) as follows:

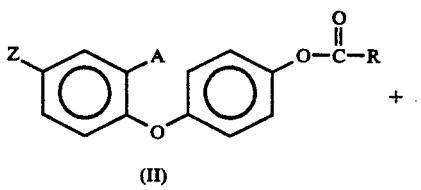

(II)

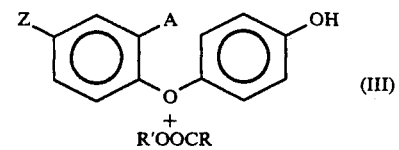

(III)
+
R'OOCR wherein

Z, A, and R are as defined hereinbefore; and

R'OH represents C-1 to C-20 primary, secondary and tertiary alcohols, preferably primary alcohols, more preferably C-1 to C-6 primary alcohols, most preferably C-6 alcohol or hexanol.

The alcohol (R'OH) is employed in amounts sufficient to convert the phenoxyphenyl ester (II) to the desired phenoxyphenol (III). Such amounts can range from an excess of alcohol to stoichiometric amounts relative to the phenoxyphenyl ester (II) such as 100–1:1 (moles alcohol:moles phenoxyphenyl ester (II)), preferably about 5–3:1.

Catalysts which can be used to transesterify the phenoxyphenyl ester (II) to the desired phenoxyphenol (III) include mineral acids such as $H_2SO_4$, HCl and $H_3PO_4$ strong organic acids such as toluenesulfonic acid and acidic ion exchange resins described hereinbefore: and preferably tetraalkyltitanate catalysts of the formula:

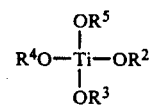

wherein $R^2$, $R^3$, $R^4$ and $R^5$ independently represent C-1 to C-6 alkyl, preferably C-4; most preferably where $R^2$, $R^3$, $R^4$ and $R^5$ each is C-4 alkyl. The catalyst is used in amounts sufficient to convert the phenoxyphenyl ester (II) to the desired phenoxyphenol (III). The amounts of catalyst can range from about 0.1 to about 10.0 percent (weight basis) based on the weight of the phenoxyphenyl ester (II); preferably from about 0.1 to about 2.0 percent; more preferably from about 0.1 to about 0.5 percent by weight.

The temperatures, pressures and times for contacting the ingredients should be sufficient to convert the phenoxyphenyl ester (II) to the desired phenoxyphenol (III). The temperatures can range from about 80° to about 150° C. Preferably the pressure employed is ambient. However, higher pressures can be employed where alcohols and low boiling point solvents are used, such as for methanol, ethanol, etc. The ingredients are contacted by mixing them for a period ranging from about 0.5 hours to 24 hours or more. The transesterification can occur in-situ where the oxidation of step (a) is carried out in the presence of an alcoholic solvent (R'OH).

The desired phenoxyphenol (III) can be recovered by distillation of excess alcohol and by-products such as alkylbenzoates formed during the reaction. Crystallization and/or filtration procedures can also be employed for recovery.

The phenoxyphenol (III) is converted to the corresponding racemic or optically active (phenoxyphenoxy)propionate by conventional techniques as follows:

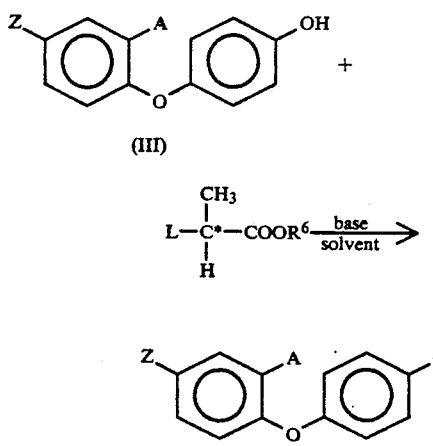

(III)

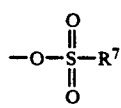

wherein Z and A are as described hereinbefore;

R[6] is hydrogen or C-1 to C-10 alkyl;

L is halogen or an alkyl or aryl sulfonate of the formula $$-O-\overset{O}{\underset{O}{\overset{\|}{S}}}-R^7$$

wherein

R[7] is C-1 to C-3 alkyl, or phenyl optionally substituted with halogen, C-1 to C-3 alkyl or nitro; and In the situation wherein, as to the phenoxyphenone of Formula 1, the phenoxyphenyl ester of Formula II and the phenoxyphenol of Formula III, Z is hydrogen, the hydrogen can be converted to bromo before proceeding further in the reaction sequence. The 4-brominated derivatives can be selectively prepared by contacting a 4-hydrogen derivative of Formula IV with bromine in the presence of a metal halide catalyst and solvent to yield the 4-bromophenoxy derivatives of Formula (V). The reaction is exemplified as follows: * repersents an assymmetric carbon atom.

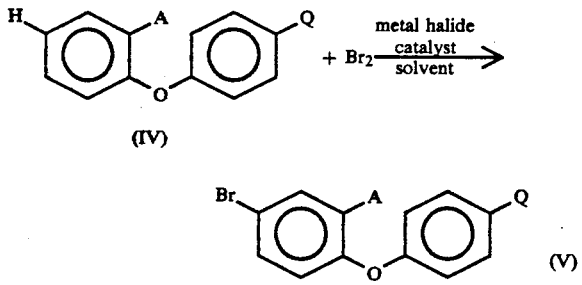

wherein

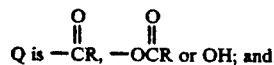

A and R are as previously defined.

The bromination occurs selectively in the ring already containing the halogen (A) and selectively in the 4-position of that ring.

Bromine (Br$_2$) is a non-metallic halogen element which has the property of being a dark, reddish-brown liquid.

The metal halide catalyst is of the formula $M^nN_n$ wherein

M is aluminum (Al), titanium (Ti), iron (Fe) or boron (B);

X is chloro, bromo or fluoro; and n is an integer which is the oxidation state of the metal.

Preferably M is aluminum; also preferred is that X is chloro or bromo and that n is 3. For titanium, preferably n is 4. Catalysts which can conveniently be employed include aluminum chloride, aluminum bromide, titanium chloride, titanium bromide, iron chloride, iron bromide and the like; aluminum chloride or bromide are usually preferred.

The metal halide catalyst is used in amounts slightly greater or much greater than the molar equivalents of 4-H-phenoxy derivative (IV) employed. A molar equivalence is defined as one mole of catalyst per mole of 4-H-phenoxy derivative (IV). The amounts of metal halide catalyst can range from about 10 to about 1.001 moles metal halide catalyst to about 1 mole 4-H-phenoxy derivative (IV), more preferably from about 1.5–1.1:1 (moles metal halide catalyst:moles 4-H-phenoxy derivative (IV)). The metal halide catalyst should be maintained anhydrous or as water-free as possible, since water can chemically react and deactivate the catalyst.

Contacting of the ingredients is performed in the presence of a solvent resistant or inert to bromination. Such inert solvents include, but are not limited to, chlorinated aliphatic hydrocarbons such as methylene chloride, carbon tetrachloride, chloroform, perchloroethylene, 1,2-dichloroethane, trichloroethylene and the like. The solvent employed can range from an amount sufficient to at least slurry the ingredients up to any amount which would homogenize the ingredients. Typically, the concentration of the 4-H-derivative (IV) is from about 5 to about 50 percent by weight of a solution containing an inert solvent; preferably from about 10 to about 20 percent by weight.

The temperatures, pressures and times employed should be sufficient to yield the desired 4-bromophenoxy derivatives of Formula (V). The temperature can range from about −30° C. to the boiling point of bromine, preferably from about 0° to about 30° C. due to the ease of handling the bromine and/or improved selectivity of bromination. The pressure can range from ambient to pressures greater than ambient, preferably ambient pressures. The times for contacting of the ingredients can vary ranging from about 15 min to about 4 to 5 hr or more. The ingredients can be contacted in any order or by any convenient means. Preferably, the 4-H-phenoxy derivative (IV), solvent and catalyst are first contacted together, followed by subsequent contacting with slow and/or continuous additions of bromine due to the evolution of HBr.

The desired 4-bromophenoxy derivative (V) can be recovered by conventional procedures such as extraction, distillation, recrystallization, filtration and the like.

The Examples which follow illustrate the present invention in a manner by which it can be practiced but, as such, should not be construed as limitations upon the overall scope of the same.

Example 1 - Preparation of 4-(2-fluorophenoxy)benzophenone by coupling 2-fluorophenol and 4-chlorobenzophenone

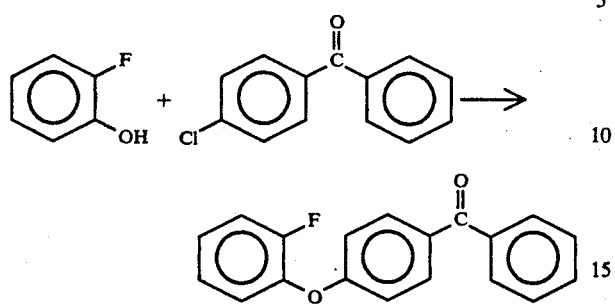

A solution of 224 grams (g) (2.00 moles) of 2-fluorophenol, 263 g of 43 percent by weight aqueous KOH (2.02 moles KOH), and one liter (L) of dimethyl sulfoxide (DMSO) was heated to 125 degrees Centigrade (° C.) and water is distilled out with the aid of a Vigreux column under reduced pressure. To the reaction mixture 433 g (2.00 moles) 4-chlorobenzophenone was then added and the resulting mixture was heated for 20 hours (hr) at 125° C. The reaction mixture was diluted with 50 milliliters (mL) of concentrated hydrochloric acid (HCl) and 1 liter of water, and then extracted with two 250 mL portions of perchloroethylene. The combined organic phases were washed with 1 liter of water and then concentrated in vacuo to afford 581.2 g of crude product. Purification by distilling out the low boiling impurities was carried out using a column packed with perforated nickel packing. Bottoms product yield was 77 percent for 452.0 g 4-(2-fluorophenoxy)benzophenone recovered, based on fluorophenol.

An analytical sample has a melting point of 50°-52°; $^{13}$C-NMR (75.5 MHz, CDCl$_3$)δ161.23 (s), 154.54 (d, JC-F-250 Hz), 142.10 (d, J=12 Hz), 137.84 (s), 132 (s), 132.24 (s), 132.09 (s), 132.03 (s), 129.74 (s), 128.20 (s), 126.10 (d, J=8 Hz), 124.96 (d, J=4 Hz), 123.03 (s), 117.31 (d, J=18 Hz), 115.82 (s); ir (neat) 1665 cm$^{-1}$(s), 1605 (s), 1510 (s), 1455 (m), 1420 (m), 1280 (s), 1230 (s).

Example 2 - Preparation of 4-(4-bromo-2-fluorophenoxy)acetophenone by coupling 4-bromo-2-fluorophenol with 4-fluoroacetophenone

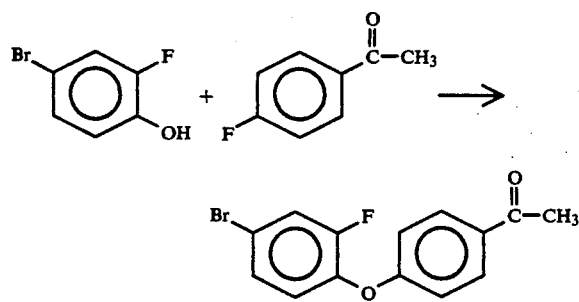

The procedure of Example 1 was employed with the following changes. Bromofluorophenol (48 g), toluene (60 mL), N-methylpyrrolidone (NMP) (50 mL), and 50 percent aqueous NaOH (17.5 g) were dried by distillation of water and toluene. Fluoroacetophenone (38.5 g) was added and the mixture was heated at 190° C. for 4.5 hr. Most of the NMP was distilled out and the residue was extracted with 100 mL of cold water and 80 mL of carbon tetrachloride (CCl$_4$). The organic phase was washed with 100 mL of water, and then concentrated in vacuo to afford 88.2 g of crude product. Vacuum distillation afforded 52 g (76% yield) of 4-(4-bromo-2-fluorophenoxy)acetophenone, having a boiling point of 161°-162° C. at 0.4 millimeters (mm) Mercury (Hg).

An analytical sample has a melting point of 51°-52°, ir (KBr) 1690 cm$^{-1}$ (s), 1605 (s), 1510 (s), 1420 (m), 1380 (s), 1290 (s), 1240 (s). Elemental analysis, calculated for C$_{14}$H$_{10}$BrFO$_2$; C, 54.37: H, 3.26. Found: C, 54.42: H, 3.27.

Example 3 - Preparation of 4-(2-fluorophenoxy)benzophenone by coupling 2-fluorophenol and 4-fluorobenzophenone

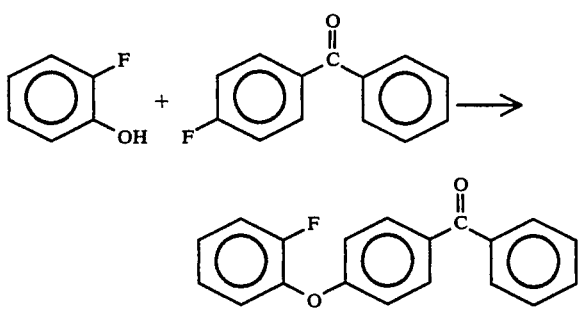

The procedure of Example 1 was employed with the following modifications.

Potassium hydroxide (12.82 g of 86.2 percent KOH: 0.197 moles) was dissolved in 11 mL of H$_2$O and added to a solution of 40 g (0.20 moles) 4-fluorobenzophenone in 100 mL of DMSO. The mixture was degassed by three times pulling a vacuum and releasing it with N$_2$. To this solution was added, slowly, 21.5 g (0.19 moles) of o-fluorophenol and 2.1 g (0.0095 moles) BHT (2,6-di-t-butyl-4-methylphenol). The bulk of the water was removed by vacuum distillation, keeping the pot temperature under 85° C. The water distillation took 2 hr and 12.2 g of distillate was collected. The reaction mixture, which analyzed at 0.8% H$_2$O was held at 80° C. for 19 additional hr, at which time conversion was approximately 99 percent. The reaction mixture was diluted with 60 mL H$_2$O, 4 mL conc. HCl, and 20 mL perchloroethylene. The aqueous phase was extracted with an additional 10 mL of perchloroethylene and the combined organic phases were washed with 30 mL H$_2$O. Solvent stripping left 59.5 g of oil, which solidified upon standing. The crude product assayed as 92.0 percent pure 4-(2-fluorophenoxy)benzophenone, for a 98 percent isolated yield.

Example 4 - Preparation of 4-(2-fluorophenoxy)benzophenone by coupling 2-fluorophenol and 4-fluorobenzophenone

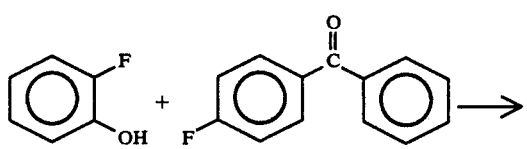

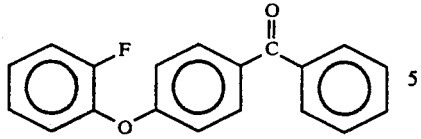

The procedure of Example 1 was employed with the following modifications.

All the components (301 g of 46 percent aqueous KOH, 501 g of fluorobenzophenone, 800 mL of DMSO, and 269 g of fluorophenol), plus 5 mole percent BHT (25 g) were mixed together under a nitrogen atmosphere and distillation of water was carried out at a maximum temperature of 80° C. Reaction continued at 70° C. for a total of 12 hr. Purification by lights distillation gave an 87 percent yield of 4-(2-fluoro-phenoxy)-benzophenone.

Example 5 - Preparation of 4-(4-bromo-2-fluorophenoxy)benzaldehyde by coupling 4-bromo-2-fluorophenol and 4-fluorobenzaldehyde

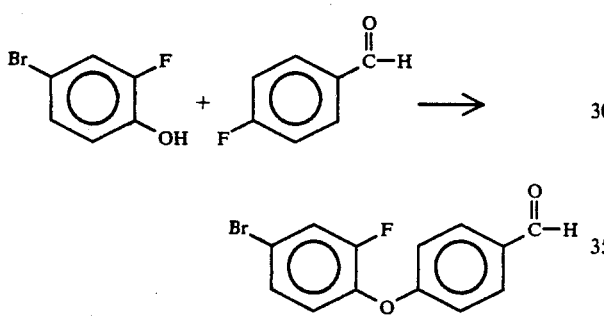

Sodium 4-bromo-2-fluorophenate was prepared by contacting 25 percent aqueous NaOH and bromofluorophenol (1.11 equivalents). The resulting solution was washed with toluene and the aqueous product layer was concentrated in vacuo. The solid product was powdered and contained 2.4 percent water. A solution of 10.0 g of the sodium bromofluorophenate in 20 mL of NMP was heated to 120° C. and 5.8 g of fluorobenzaldehyde was added. After the mixture was heated at 180° C. for 4 hr, it was diluted with 100 mL of 10 percent HCl and extracted with CH$_2$Cl$_2$. The organic layer was washed with 100 mL of water and then concentrated in vacuo. Vacuum distillation of the crude product afforded 10.4 g of 4-(4-bromo-2-fluorophenoxy)benzaldehyde, bp 145°-152°/0.6 mm Hg.

Example 6 - Preparation of 4-(4-bromo-2-fluorophenoxy) benzophenone via bromination of 4-(2-fluorophenoxy)benzophenone

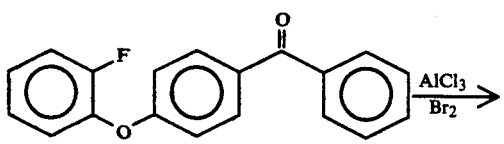

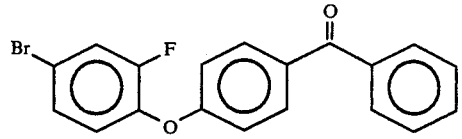

To a slurry of 295 g of AlCl$_3$ powder (2.22 moles) in 1.5 liter of methylene chloride (CH$_2$Cl$_2$) was added 581 g of fluorophenoxybenzophenone (2.00 moles). After the mixture became homogeneous, a solution of 329 g of bromine (2.06 moles) in 300 mL of CH$_2$Cl$_2$ was added continuously over a period of 3 hr while maintaining a reaction temperature of 30° C. The reaction mixture was continuously added to 2.2 kg of ice water. The organic phase was separated and washed with 1 liter of water.

The resulting solution of 4-(4-bromo-2-fluorophenoxy)benzophenone (~95% purity by capillary gas chromatographic analysis) in CH$_2$Cl$_2$ was carried forward to the next step (Example 10). A purified sample has a melting point of 91.0°-92.5° C.; ir (KBr) 1650 (s), 1610 (s), 1590 (s), 1500 (s), 1290 (s), 1275 (s), 1220 (s). Elemental analysis, calculated for C$_{19}$H$_{12}$BrFO$_2$: C, 61.46: H, 3.26. Found: C, 61.61: H, 3.32.

Example 7 - Preparation of 2-fluorodiphenyl oxide

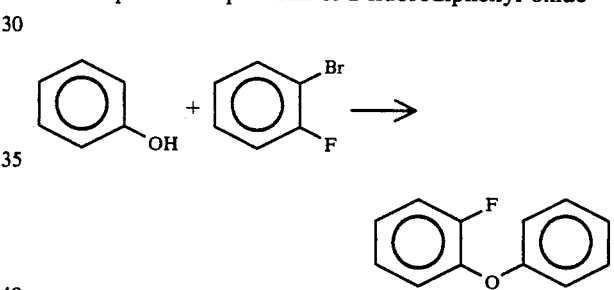

A mixture of phenol (47.5 g; 0.5 moles), butylated hydroxytoluene (BHT: 2.0 g: 0.009 moles), diglyme (200 mL) and 25 percent NaOCH$_3$/CH$_3$OH (111.8 g; 0.5 moles) in a nitrogen purged flask was heated to 120° C. to remove the methanol (104.4 g distillate). After cooling to 75° C., o-bromofluorobenzene (134 g; 0.77 moles) copper metal (0.5 g; 0.008 moles) and cuprous chloride (1.9 g: 0.019 moles) were added and the mixture was heated at 125° C. After 20 hr, gas chromatographic analysis indicated 50 percent conversion and the reaction mixture was quenched with 40 mL of water and 10 mL of concentrated hydrochloric acid. After filtration, the organic phase was separated and distilled to give three cuts: 60 g of diglyme and o-bromofluorobenzene: 27.8 g of primarily phenol: and 49.5 g of 98 percent pure 2-fluorodiphenyl oxide.

Example 8 - Preparation of 4-(4-bromo-2-fluorophenoxy)-3',5'dichlorobenzophenone

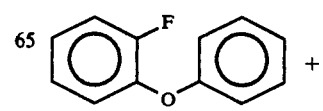 +

-continued

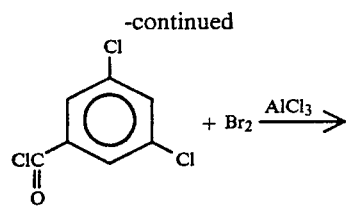

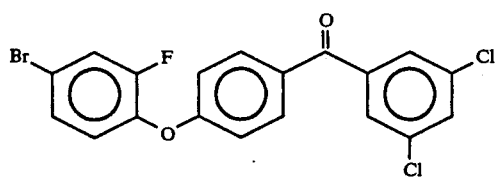

To a mixture of 1.30 g of 2-fluorodiphenyl oxide, 1.49 g of 3,5-dichlorobenzoyl chloride, and 4 mL of carbon tetrachloride was added 1.0 g of aluminum chloride in portions over 20 min with ice-water cooling. After two hr, a solution of 1.2 g of bromine in 1 mL of carbon tetrachloride was added over 30 min with ice-water cooling. After an additional 3.5 hr, the reaction mixture was poured into water and extracted with carbon tetrachloride. The combined organic phase was washed with dilute sodium thiosulfate solution and concentrated in vacuo, yielding 3.0 g. A portion of this product was recrystallized from carbon tetrachloride (mp 126.5°–128.5° C.).

Example 9 - Oxidation of 4-(4-bromo-2-fluorophenoxy)-3′,5′-dichlorobenzophenone

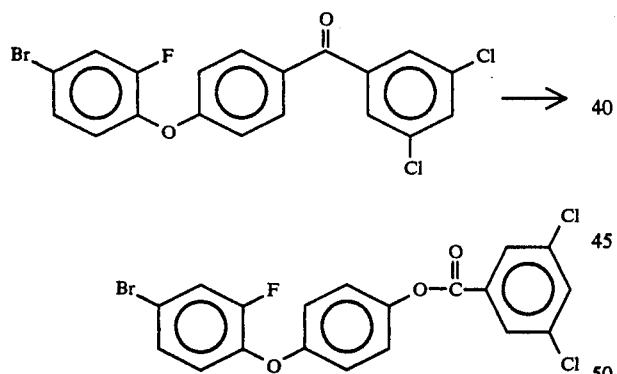

To a slurry of 1.0 g of 4-(4-bromo-2-fluorophenoxy)-3′,5′-dichlorobenzophenone in 6 mL of acetic acid was added 1.6 g of sulfuric acid and the mixture was heated to 50° C. Hydrogen peroxide (70%, 0.20 g) was added over 0.5 hr. Heating continued for 7 hr and then the reaction mixture was allowed to stir for 2.5 days at ambient temperature. At this time, the reaction mixture was partitioned between methylene chloride and water, and the organic phase was concentrated in vacuo to give 0.93 g of 4-(4-bromo-2-fluorophenoxy)phenyl-3′,5′-dichlorobenzoate as a yellow-white solid which was 96 area % pure by capillary GC analysis. The structure of this product was confirmed by performing a basic hydrolysis (25% aq KOH, ethanol, 70° C., 3 hr) and obtaining 4-(4-bromo-2-fluorophenoxy)phenol along with 3,5-dichlorobenzoic acid.

Example 10 - Preparation of 4-(4-bromo-2-fluorophenoxy)phenyl benzoate with peracetic acid generated in situ from hydrogen peroxide and acetic acid

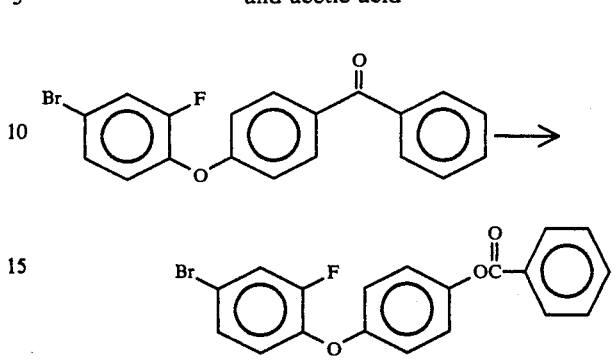

Most of the $CH_2Cl_2$ was stripped from one-half of the solution containing 4-(4-bromo-2-fluorophenoxy)benzophenone from Example 6. To the resulting crude 4-(4-bromo-2-fluorophenoxy)benzophenone (370 g) was added 1086 mL of glacial acetic acid and then 186 mL of concentrated sulfuric acid. The reaction mixture was heated at 50° C. and 58 g of 70 percent aqueous hydrogen peroxide was added over a period of 2.5 hr. After 7 hr, one liter of water was added and the mixture was then extracted with 200 mL of perchloroethylene. The organic phase was then washed successively with 500 mL of 10 percent aqueous sodium carbonate and 500 mL of 1 percent aqueous sodium bisulfite. After removal of solvent, the crude 4-(4-bromo-2-fluorophenoxy)phenyl benzoate weighed 360.1 g (90% purity, 88% yield). A purified sample has a melting point of 72°–75° C., ir (KBr) 1745 cm$^{-1}$ (s), 1600 (m), 1505 (s), 1390 (s), 1205 (s), 1100 (s), 1080 (s). Elemental analysis, calculated for $C_{19}H_{12}BrFO_3$: C, 58.91; H, 3.13. Found: C, 58.85; H, 3.20.

Example 11 - Preparation of 4-(4-bromo-2-fluorophenoxy)phenol from 4-(4-bromo-2-fluorophenoxy)acetophenone and peracetic acid

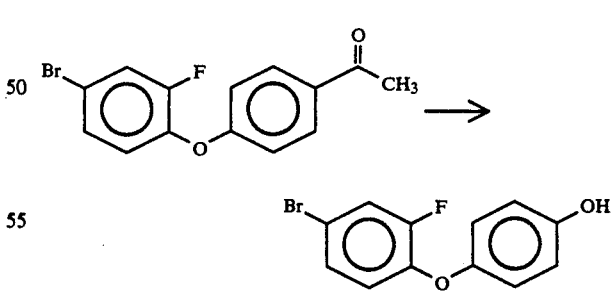

To a solution of 6.3 g of 4-(4-bromo-2-fluorophenoxy)acetophenone, 20 g of acetic acid, and 1.1 g of concentrated sulfuric acid was added 1.4 g of 70 percent hydrogen peroxide over a period of 20 min. After one day at ambient temperature, the reaction mixture was poured into 150 mL of ice-water, and the solid which formed was collected by suction filtration. After air drying 5.4 g of crude 4-(4-bromo-2-fluorophenoxy)phenol of 86% purity (82% yield) was obtained.

Example 12 - Preparation of 4-(4-bromo-2-fluorophenoxy)phenol by base hydrolysis of 4-(4-bromo-2-fluorophenoxy)phenyl benzoate

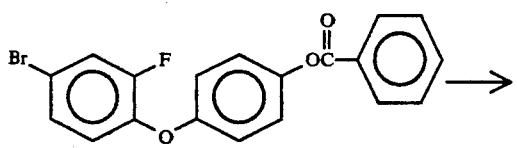

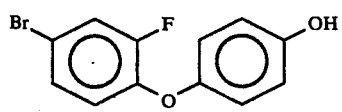

The crude bromofluorophenoxyphenyl benzoate (99 g) from an oxidation reaction similar to Example 10 was slurried in 500 mL of methanol and 350 g of 11 percent aqueous KOH was added while maintaining a temperature of 18°-27° C. After 11 hr, the reaction mixture was diluted with one liter of water and the pH was adjusted to 7 with concentrated HCl. Methylene chloride (20 mL) was added, the phases separated, and the solvent removed in vacuo to give 68.3 g of 4-(4-bromo-2-fluorophenoxy)phenol (95% purity, 94% yield). A purified sample has a melting point of 83.5°-85.0° C: $^{13}$C-NMR (20.15 MHz, CDCl$_3$)δ153.6 (d, $J_{C-F}$=253 Hz), 151.7 (s), 150.1 (s), 144.6 (d, J=11 Hz), 127.6 (d, J=4 Hz), 121.2 (s), 120.4 (d, J=21 Hz), 119.6 (s), 116.5 (s), 115.1 (d, J=8 Hz).

Example 13 - Preparation of 4-(4-bromo-2-fluorophenoxy)phenol by alcoholysis (transesterification) of 4-(4-bromo-2-fluorophenoxy)phenyl benzoate with hexanol and tetrabutyltitanate

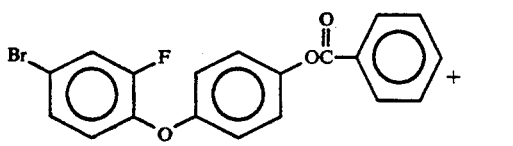

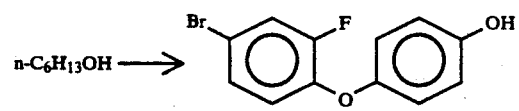

A solution of crude 4-(4-bromo-2-fluorophenoxy)-phenyl benzoate (360 g) and hexanol (360 g) was dried by distilling out 30 mL of hexanol and then 0.8 g of tetrabutyltitanate was added and the reaction mixture was heated for 38 hr at 115° C. A 93 g sample was removed at this time. Water (0.2 g) was then added, followed by removal of unreacted hexanol and the by-product hexyl benzoate via vacuum distillation through a five tray Oldershaw column. Distillation was continued to produce 183 g of 4-(4-bromo-2-fluorophenoxy)-phenol of 97% purity (86% yield).

Example 14 - Preparation of 4-(4-bromo-2-fluorophenoxy)phenol from 4-(4-bromo-2-fluoro-phenoxy)acetophenone and hydrogen peroxide

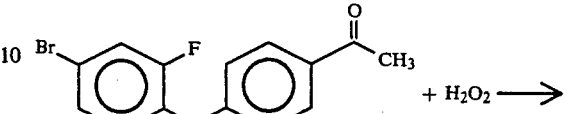

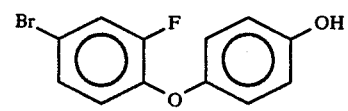

To a solution of 0.70 g of bromofluoroacetophenone, 4 mL of methanol, and 0.60 g of concentrated sulfuric acid was added 0.30 g of 70 percent hydrogen peroxide. This solution was heated for 3 hr at 50° C. and then diluted with 5 mL of CH$_2$Cl$_2$ and washed successively with dilute aqueous Na$_2$SO$_3$ (10 mL) and water (10 mL). Solvent was removed in vacuo to give 0.58 g of 4-(4-bromo-2-fluorophenoxy)phenol of 62 percent purity by capillary gas chromatographic analysis.

Example 15 - Preparation of 4-(2-fluorophenoxy)phenyl benzoate from 4-(2-fluorophenoxy)benzophenone

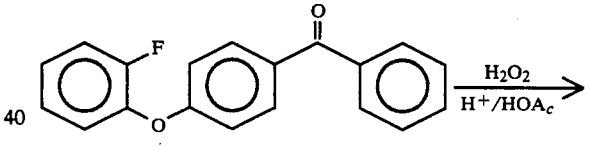

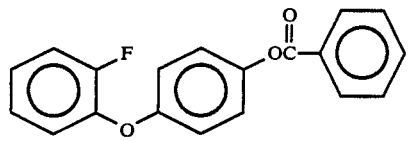

To a 2 liter flask equipped with a thermometer, stirrer and condenser was added 300 g (1.01 moles) of 4-(2-fluorophenoxy)benzophenone, 900 g (15 moles) of acetic acid and 236.2 g (2.4 moles) of sulfuric acid. The reaction mixture was heated to 40° C. and 60 g (1.24 moles) of 70 percent hydrogen peroxide was added over 140 min while maintaining the temperature between 39°-41° C.; an air gun was used to cool the exothermic reaction. After about half of the hydrogen peroxide had been added, the product began to crystallize. After addition of the hydrogen peroxide was complete, the temperature was held at 40° C. for 7 hrs. The reaction mixture was cooled to ambient temperature and was filtered. The solids were washed twice with 350 mL of water. A small portion of the solid 4-(2-fluorophenoxy)-phenyl benzoate was dried: m.p. 99.5°-101.5° C.

Example 16 - Preparation of 4-(2-fluorophenoxy)phenol by base hydrolysis of 4-(2-fluorophenoxy)phenyl benzoate

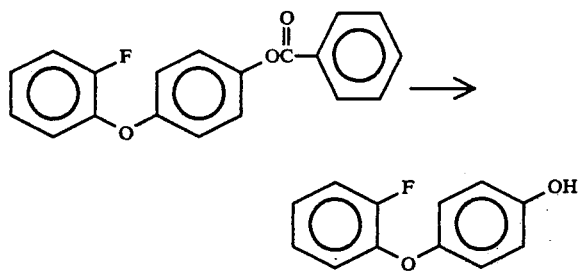

The wet 4-(2-fluorophenoxy)phenyl benzoate of Example 15 was dissolved in approximately 575 mL of perchloroethylene at 60° C. and was rapidly mixed with 600 g of 25 percent sodium hydroxide. The reaction mixture was heated to 80° C. and monitored by gas chromatography until the hydrolysis was complete. After completion, the reaction mixture was cooled to 60° C. and diluted with 250 mL of water. The phases were separated and the aqueous phase was twice washed with 100 mL of perchloroethylene to remove unreacted starting material and other neutral materials from the hydrolysis products which remain in the aqueous phase.

Approximately 660 mL of perchloroethylene was added to the aqueous phase and, while still at 60° C., the pH was slowly adjusted to about 5.9 with about 180 mL of concentrated hydrochloric acid. The organic phase was separated, cooled to about 40° C. and mixed with 250 mL of water. The pH of the resulting mixture was adjusted to about 7.8 with about 20 g of 25 percent sodium hydroxide solution. The organic phase containing the 4-(2-fluorophenoxy)phenol was separated from the aqueous phase containing sodium benzoate. The solvent can be evaporated from the organic phase to give 193.5 g of 4-(2-fluorophenoxy)phenol, m.p. 81.5°-82° C., or the perchloroethylene extraction solution can be carried forward for bromination without removal of the solvent.

Example 17 - Preparation of 4-(2-fluorophenoxy)acetophenone by the coupling of 2-fluorophenol with 4-fluoroacetophenone

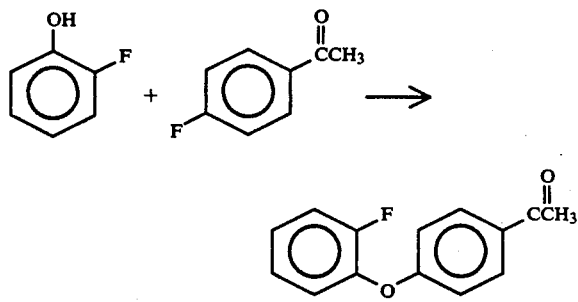

A 1-1 flask, equipped with a thermometer, stirrer, and distillation column and head, was loaded with 123.9 g (1.03 moles) of 45.6 percent KOH and 500 mL DMSO. The system was purged by pulling a vacuum and releasing it with N₂ four times. Butylated hydroxy mole) were then carefully added (10°-20° C. exotherm). The system was put under vacuum and the bulk of the water removed by distillation. The vacuum was adjusted so as to maintain the pot temperature under 80°-85° C. The distillation was stopped when the head temperature reached about 72° C./12 mm, after about 2 hours and after 114 g of water and DMSO were collected. Analysis showed the water level in the pot to be 0.3 percent. To the mixture was added 144 g (1.04 moles) of 4-fluoroacetophenone. The mixture was reacted at 80° C. for 25 hours and was then diluted with 300 mL water, 25 mL conc. HCl, and 75 mL perchloroethylene. The resulting aqueous phase was extracted with 15 mL perchloroethylene. These extractions had to be done warm to keep the KF from coming out of solution. The combined organic phases were washed with 150 mL of acidified water and then were lights stripped, first on a rotavap to remove most of the solvent and then using a vigreux column. When the pot reached 200° C. and the head 150°-160° C./5 mm the distillation was stopped. The overheads, excluding perchloroethylene, weighed 20 g, of which only 2-3 percent was product. The bottoms, a yellow oil which solidified upon standing, weighed 220 g and assayed at 98+ percent. Purified product had a melting point of 58°-60° C.

Example 18 - Preparation of 4-(2-fluorophenoxy)phenol by the H₂O₂ oxidation of 4-(2-fluorophenoxy)acetophenone

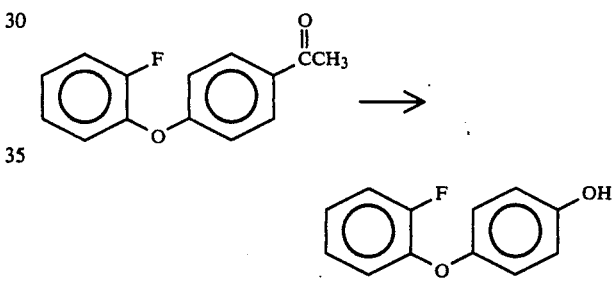

In a 1-1 flask equipped with a thermometer, stirrer, and drying tube was placed 210 g (0.9 moles) 4-(2-fluorophenoxy)acetophenone, 210 g AcOH, and 31.7 g (0.32 moles) H₂SO₄. The solution was cooled and held at 16° C. To this solution was added 90.6 g (1.85 moles) of 70 percent H₂O₂ over 4 hours. The mixture was reacted for a total of 30 hours before diluting with 850 mL of 10 percent NaHSO₃ and 200 mL of perchloroethylene. The bisulfite addition was exothermic. The aqueous phase was extracted with 50 mL perchloroethylene. The combined organic phases were reacted with 350 g of 25 percent NaOH for 45 min at 40°-60° C. The reaction mixture was then diluted with 700 mL water and phase separated. The aqueous phase was extracted with 2x70 mL perchloroethylene. The pH of the aqueous phase was adjusted to about 2 with conc. HCl, while warm, to cause the phenol to oil out. The oil was separated and the aqueous layer was extracted with 70 mL perchloro-ethylene. The combined organics were distilled first on a rotavap to remove perchloroethylene and then using a vigreux column to purify the product. The main product cut (129 g) was collected at a head temperature of 145°-150° C./1.3 mm and assayed at 97+ percent. The following cut (19.5 g) at 150°-160° C. assayed at 85 percent 4-(2-fluorophenoxy)phenol and 11 percent 4-(2-fluorophenoxy)benzoic acid. This cut could be recycled to the next distillation.

Example 19-Preparation of 4-(4-bromo-2-fluorophenoxy)phenol from 4-(2-fluorophenoxy)phenol and bromine

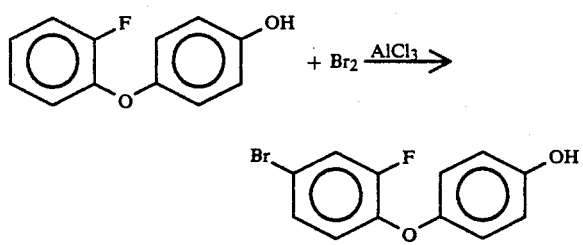

To a 250 mL flask equipped with a nitrogen purge, mechanical stirrer, thermometer, condenser and gas scrubber was added 100 mL of perchloroethylene and 16 g (0.12 moles) of AlCl$_3$. The slurry was heated to 60° C. and a solution of 20.4 g (0.10 moles) of 4-(2-fluorophenoxy)phenol in 100 mL of perchloroethylene was added slowly. During the addition HCl gas was given off as the complex with AlCl$_3$ formed. At the end of the addition the temperature was 75° C. The clear, rose-colored solution was cooled to 13° C. with an ice-water bath. To the cooled, rapidly stirred solution was added a total of 16 g (0.1 moles) of liquid bromine dropwise over a 1 hour period at 12°-16° C. After stirring for an additional 30 min, 80 mL of water and 50 mL of methylene chloride were added and the layers were separated. The organic phase was further extracted with 2-50 mL portions of 10% aqueous HCl and then 2-50 mL portions of water. Stripping the solvent under vacuum gave 27.9 g (98.5%) yield of crude product. This crude product was recrystallized from 20 mL of perchloroethylene to give after precipitation, filtration, and drying, 24.2 g (88% yield) of 4-(4-bromo-2-fluorophenoxy)phenol, mp 81-83.5. The identity to the product was confirmed by C$^{13}$ NMR, IR and mixed mp with an authentic sample.

What is claimed is:

1. A method of preparing a phenoxyphenol compound of the formula

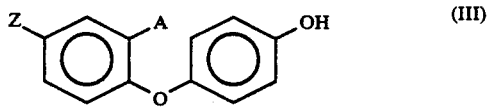

wherein
Z is Br of H; and
A is halogen
comprising:
  (a) contacting a phenoxyphenone compound of the formula

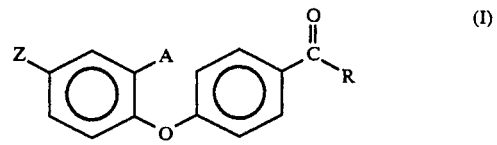

wherein
Z and A are as defined before and
R is phenyl or substituted phenyl of the formula

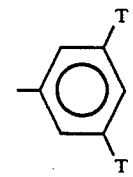

wherein
T is independently H or halogen
with peroxide in the presence of an acid catalyst to form a phenoxyphenol ester of the formula

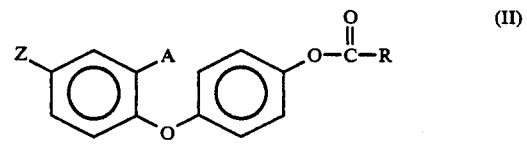

wherein
Z, A, and R are as previously defined; and
  (b) converting the phenoxyphenyl ester (II) to the phenoxyphenol (III).

2. The method of claim 1, wherein the phenoxyphenyl ester is converted to the phenoxyphenol by alcoholysis with an alcohol in the presence of a transesterification catalyst.

3. The method of claim 2 wherein the transesterification catalyst is a tetraalkyltitanate.

4. The method of claim 1 wherein the phenoxyphenyl ester is converted to the phenoxyphenol by hydrolysis in the presence of an acid.

5. The method of claim 1 wherein the phenoxyphenyl ester is converted to the phenoxyphenol by hydrolysis in the presence of a base followed by neutralization with an acid.

6. The method of claim 1 wherein R is phenyl.

7. The method of claim 6 wherein A is fluorine or chlorine.

8. The method of claim 6 wherein Z is bromine and A is fluorine.

9. The method of claim 6 wherein Z is hydrogen and A is fluorine.

* * * * *